United States Patent
Noriega

[11] Patent Number: 6,059,767
[45] Date of Patent: May 9, 2000

[54] STEERABLE UNITARY INFUSION CATHETER/GUIDE WIRE INCORPORATING DETACHABLE INFUSION PORT ASSEMBLY

[75] Inventor: Gerardo V. Noriega, Mt. View, Calif.

[73] Assignee: Norborn Medical, Inc., Mountain View, Calif.

[21] Appl. No.: 09/030,657

[22] Filed: Feb. 25, 1998

[51] Int. Cl.[7] .................................................. A61M 25/00
[52] U.S. Cl. ............................ 604/523; 604/95; 604/528
[58] Field of Search ............................ 604/264, 95, 525, 604/528, 523, 532–535, 500, 502, 506, 507, 508, 513; 128/772

[56]  References Cited

U.S. PATENT DOCUMENTS

| | | |
|---|---|---|
| 4,068,660 | 1/1978 | Beck . |
| 4,368,730 | 1/1983 | Sharrock . |
| 4,377,169 | 3/1983 | Banks . |
| 4,471,779 | 9/1984 | Antoshkiw et al. . |
| 4,490,421 | 12/1984 | Levy . |
| 4,516,972 | 5/1985 | Samson . |
| 4,534,363 | 8/1985 | Gold . |
| 4,538,622 | 9/1985 | Samson et al. . |
| 4,545,390 | 10/1985 | Leary . |
| 4,548,206 | 10/1985 | Osborne . |
| 4,554,929 | 11/1985 | Samson et al. . |
| 4,573,470 | 3/1986 | Samson et al. . |
| 4,586,923 | 5/1986 | Gould et al. . |
| 4,601,705 | 7/1986 | McCoy . |
| 4,613,385 | 9/1986 | Thomas et al. . |
| 4,616,653 | 10/1986 | Samson et al. . |
| 4,619,263 | 10/1986 | Frisbie et al. . |
| 4,641,654 | 2/1987 | Samson et al. . |
| 4,646,719 | 3/1987 | Neuman et al. . |
| 4,646,742 | 3/1987 | Packard et al. . |
| 4,676,249 | 6/1987 | Arenas et al. . |
| 4,708,717 | 11/1987 | Deane et al. . |
| 4,708,718 | 11/1987 | Daniels . |
| 4,715,378 | 12/1987 | Pope, Jr. et al. . |
| 4,717,387 | 1/1988 | Inoue et al. . |
| 4,719,924 | 1/1988 | Crittenden et al. . |
| 4,721,117 | 1/1988 | Mar et al. . |
| 4,723,936 | 2/1988 | Buchbinder et al. . |
| 4,739,768 | 4/1988 | Engelson . |
| 4,763,647 | 8/1988 | Gambale . |
| 4,767,400 | 8/1988 | Miller et al. . |
| 4,779,628 | 10/1988 | Machek . |
| 4,798,598 | 1/1989 | Bonello et al. . |
| 4,832,047 | 5/1989 | Sepetka et al. . |
| 4,846,186 | 7/1989 | Box et al. . |
| 4,899,787 | 2/1990 | Ouchi et al. . |
| 4,906,241 | 3/1990 | Noddin et al. . |
| 4,925,445 | 5/1990 | Sakamoto et al. . |
| 4,953,553 | 9/1990 | Tremulis . |
| 5,021,044 | 6/1991 | Sharkawy . |
| 5,041,085 | 8/1991 | Osborne et al. . |
| 5,059,851 | 10/1991 | Corl et al. . |
| 5,107,852 | 4/1992 | Davidson et al. . |
| 5,165,421 | 11/1992 | Fleischhacker et al. . |
| 5,176,661 | 1/1993 | Evard et al. . |
| 5,178,158 | 1/1993 | de Toledo . |
| 5,184,627 | 2/1993 | de Toledo . |
| 5,195,971 | 3/1993 | Sirhan . |
| 5,209,727 | 5/1993 | Radisch, Jr. et al. . |
| 5,211,636 | 5/1993 | Mische . |
| 5,217,482 | 6/1993 | Keith . |
| 5,250,034 | 10/1993 | Appling et al. . |
| 5,267,979 | 12/1993 | Appling et al. . |
| 5,306,252 | 4/1994 | Yutori et al. . |
| 5,345,945 | 9/1994 | Hodgson et al. . |
| 5,462,523 | 10/1995 | Samson et al. . |
| 5,484,407 | 1/1996 | Osypka . |
| 5,569,197 | 10/1996 | Helmus et al. . |
| 5,571,085 | 11/1996 | Accisano, III . |
| 5,591,142 | 1/1997 | Van Erp . |
| 5,606,981 | 3/1997 | Tartacower et al. . |
| 5,611,777 | 3/1997 | Bowden et al. . |

*Primary Examiner*—John D. Yasko
*Attorney, Agent, or Firm*—Townsend and Townsend and Crew LLP

[57] ABSTRACT

Medical guidewires and catheters include tubular bodies having coils at their distal ends to permit steering through the vasculature. The guidewires and catheters are useful for delivering fluids to a target site, draining body fluids from a target site, and are particularly useful for the infusion of medicaments to sites within the body.

35 Claims, 6 Drawing Sheets

STEERABLE UNITARY INFUSION CATHETER/GUIDE WIRE INCORPORATING DETACHABLE INFUSION PORT ASSEMBLY

BACKGROUND OF THE INVENTION

1. Field of the Invention

This invention relates to guide wires and catheters or the type used by the medical profession for infusion or medicaments to a tissue site within the body and to catheters of the type used to drain body fluids from tissue sites within the body, and more particularly relates to an improved steerable catheter that functions also as a guide wire and which can be navigated through tortuous pathways of small vasculatures for use in the treatment of and/or diagnostic evaluation of a target tissue site accessible through such small vasculatures and the tortuous pathways they present.

2. Description of the Prior Art

A preliminary palatability and novelty search in connection with this invention has revealed the existence of the following U.S. Pat. Nos.:

| | | |
|---|---|---|
| 1,790,244 | 4,068,660 | 4,368,730 |
| 4,377,169 | 4,471,779 | 4,490,421 |
| 4,534,363 | 4,545,390 | 4,548,206 |
| 4,554,929 | 4,573,470 | 4,586,923 |
| 4,601,705 | 4,613,385 | 4,616,653 |
| 4,619,263 | 4,641,654 | 4,646,719 |
| 4,646,742 | 4,676,249 | 4,708,717 |
| 4,719,924 | 4,715,378 | 4,717,387 |
| 4,721,117 | 4,723,936 | 4,739,768 |
| 4,763,647 | 4,767,400 | 4,779,628 |
| 4,798,598 | 4,832,047 | 4,846,186 |
| 4,899,787 | 4,906,241 | 4,925,445 |
| 4,953,553 | 5,021,044 | 5,041,085 |
| 5,059,851 | 5,107,852 | 5,165,421 |
| 5,176,661 | 5,178,158 | 5,184,627 |
| 5,195,971 | 5,209,727 | 5,211,636 |
| 5,250,034 | 5,267,979 | 5,306,252 |
| 5,345,945 | 5,462,523 | 5,569,197 |
| 5,571,085 | 5,591,142 | 5,606,981 |
| | 5,611,777 | |

The steerable infusion catheter/guide wire forming the subject matter of the invention disclosed and claimed herein provides important improvements over current conventional prior art infusion catheters that, because of their design, require utilization or a separate prior-inserted guide wire to navigate a tortuous pathway to a specific tissue site within the body. Such conventional prior art infusion catheters possess limited mechanical and functional performance characteristics in terms of torqueability, penetration or "pushability", limited maneuverability and low bursting strengths. The unitary steerable infusion catheter/guide wire of the present invention obviates the enumerated limitations of conventional infusion catheters and conventional guide wires.

Accordingly, it is one of the important objects of the present invention to provide a unitary steerable infusion catheter/guide wire that obviates a separate guide wire, and which incorporates an infusion port assembly sealingly mounted on the catheter/guide wire manipulable to selectively and controllably rotate the catheter/guide wire unitary structure.

Another object of the invention is the provision of a unitary steerable infusion catheter/guide wire structure that incorporates a metallic cannula segment that is flexible over its entire length yet which possesses sufficient columnar strength to sustain the force that is necessary to effect penetration of the catheter/guide wire through small vasculatures.

A still further object of the invention is the provision of a unitary steerable infusion catheter/guide wire that possesses a bursting strength exceeding 250 psi.

Yet another object of the invention is the provision of a unitary steerable infusion catheter/guide wire that as a single unit can perform the functions of a separate catheter and a separate guide wire in cooperative association with an appropriate superimposed catheter.

A still further object of the invention is the provision of a unitary steerable infusion catheter/guide wire in sealing association with an infusion port assembly that in combination possess infusion capabilities for the delivery of therapeutic and/or diagnostic materials to an anatomical site, accessed via the general vasculature and advanced through lumens of less than 2 mm in diameter.

A still further object of the invention is the provision of a unitary steerable infusion catheter/guide wire structure which largely solves or avoids problems inherent with conventional prior art separate guide wire and infusion catheter assemblies.

Yet another important object of the invention is the provision of a unitary steerable infusion catheter/guide wire that incorporates a detachable infusion port assembly manipulable to sealingly engage the metallic cannula segment of the infusion catheter/guide wire to facilitate rotation of the catheter/guide wire to more easily enable navigation of the distal end of the catheter/guide wire to an anatomical site within the body and the infusion under pressure or a fluid or fluid-like medicament into the tissue at the site.

A still further object of the invention is the provision of a unitary steerable infusion catheter/guide wire structure incorporating a flexible distal end segment provided with a non-metallic enveloping sleeve that facilitates passage of the distal end segment through tortuous pathways of small vasculatures.

Yet another object of the invention is the provision of a unitary steerable infusion catheter/guide wire incorporating a flexible distal end segment including a pair of axially aligned interconnected transversely -flexible metallic coils incorporating means enabling selective flexure of the flexible distal end segment to define a curve having a selected radius and retention of the curve during navigation or the distal end segment through small vasculatures.

Still another object of the invention is the provision of a combined-function steerable infusion catheter/guide wire structure incorporating a distal end segment enabling dispersion of fluid or fluid like medicaments axially and transversely of the longitudinal axis of the catheter.

A still further object of the invention is the provision of a unitary steerable infusion cathether/guide wire structure which, when used to function as a guide wire for a superimposed catheter, may be coated with a lubricious layer of friction-reducing material such as a silicon-based lubricant or a hydrophilic layer to facilitate superimposition of a catheter over the flexible yet steerable infusion catheter/guide wire structure.

Yet another object of the invention is the provision of a unitary structure that may selectively function as both a steerable infusion catheter/guide wire structure and/or a hollow guide wire, and which may be coated with a selected thrombolitic agent or agents, such as heparin, to minimize the possibility of thrombus formation during use in a procedure.

The invention possesses other objects and features of advantage, some of which, with the foregoing, will become apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the steerable Infusion catheter/guide wire assembly of the invention comprises a cooperative assembly of three primary segments, namely, a detachable infusion port segment, a unitary elongated steerable metallic cannula segment symmetrical about a longitudinal axis and having the characteristics of flexibility, kink resistance, superelasticity and shape memory so that it may function selectively as both a catheter and a guide wire, and a distal flexible segment embodying means for selectively shaping the configuration of the flexible segment and optionally incorporating dispersion apertures or ports that are axially aligned with the longitudinal axis of the catheter, or possess axes transverse to the longitudinal axis of the catheter. The detachable infusion port segment comprises a three-part assembly selectively detachably and sealingly engaging the outer periphery of the elongated cannula segment adjacent one end thereof to enable selective rotation of the cannula and the flexible distal end segment attached thereto to facilitate navigation of the flexible distal end segment through tortuous vasculatures, and facilitate the injection of fluid and/or fluid-like medicaments to a tissue site, or the recovery therefrom of fluid or fluid-like substances. Means are incorporated in the flexible distal end segment enabling selective curvature thereof to facilitate navigation of the distal segment through tortuous pathways defined by small vasculatures.

DESCRIPTION OF THE PREFERRED EMBODIMENT

In terms of greater detail, as indicated above, conventional prior art infusion catheters are frequently manufactured from materials that have little or no torqueability, thus preventing the catheter per se from being rotated for navigational purposes through the small vasculatures to reach a selected tissue site, thus requiring the use of a separate guide wire. Additionally, again because or the materials generally used to fabricate the catheter, once inserted into an artery, it cannot be "pushed" along the artery because it lacks columnar strength to overcome the frictional resistance to the passage of the distal end of the catheter along the artery. Still further, because of the nature of the materials from which catheters are generally fabricated, the catheter posseses low bursting strength, usually less than 250 psi, thus limiting the amount of pressure that may be applied to effect dispersion of fluid and/or near-fluid medicaments at a selected tissue site within the body.

Due to these limited performance characteristics, prior art catheters are used in cooperative combination with conventional prior art guide wires. Typically, these conventional guide wires are used in two different aspects. In one aspect, the guide wire as a separate element is inserted into the general vascular anatomy by torquing and pushing the wire intravascularly to reach small vessel sites within the body.

The columnar strength, i.e., its resistance to bending, enables such intravascular penetration or passage of the wire until the distal end is positioned at a selected tissue site. A catheter may then be inserted over the guide wire and slid along the wire until its distal end is positioned at the selected tissue site.

In a second aspect, the guide wire is initially inserted into the catheter to form an assembly, the guide wire providing columnar strength to the catheter, and the assembly of guide wire and catheter is then torqued and pushed intravascularly to reach small vessel sites within the body. Due to the catheter design, the guide wire is needed to provide columnar strength to the catheter and is therefore used to guide and position conventional prior art catheters at target tissue sites. However, the simultaneous use of both a separate infusion catheter and a separate guide wire assembly increases the likelihood of masking or losing the target site position sought to be reached, thus delaying the performance or completion of any therapeutic and/or diagnostic procedure.

The unitary steerable infusion catheter/guide wire of the instant invention functions as a self-guided catheter, and does not require a separate guide wire. The structural design of the unitary steerable infusion catheter/guide wire forming the subject matter of the invention disclosed and illustrated herein provides the maneuverability, torqueability, and columnar strength or "pushability" characteristics necessary for accurately positioning the distal end of the unitary steerable catheter/guide wire at specific anatomical sites, all without the use of a separate guide wire. The structural design of the instant invention also allows the steerable catheter/guide wire to be guided from an external body tissue site to an internal body tissue site to allow: 1) administration of therapeutic and/or diagnostic materials [fluid of fluid-like mediums], 2) positioning of intravascular catheter [i.e., balloon dilation catheters, atherectomy catheters, rotational catheters, extractional catheters and traditional guiding catheters], 3) focusing an external source of radiation at a desired anatomical site, and/or 4) marking sites for surgical excision. From the above, it will be understood that the unitary steerable infusion catheter/guide wire of the instant invention possesses a versatility not found in prior art catheters, and that the functions indicated above are enabled by use of the subject invention while maintaining target site positioning and without the need of a secondary device such as a guide wire/catheter assembly.

Referring to the drawings, particularly FIGS. 1–5, it will there be seen that the steerable infusion catheter/guide wire assembly of the invention is designated generally by the numeral 2. The catheter/guide wire assembly includes a detachable infusion port sub-assembly designated generally by the numeral 3. An elongated flexible metallic cannula designated generally by the numeral 4 has its proximal end portion 6 inserted into and sealingly engaged detachably to the infusion port sub-assembly. This sealing interconnection enables injection under pressure of various fluid and/or fluid-like medicaments into the open end 7 of the cannula, for passage therethrough and dispersion from the catheter's flexible distal segment designated generally by the numeral 8, and shown with its proximal end portion connected to the distal end portion of the elongated flexible metallic cannula so as to receive therefrom fluid and/or fluid-like medicaments under pressure for dispersion at a selected tissue site. Alternatively, the catheter may be utilized to withdraw body fluids from internal tissue sites.

Figure 2:
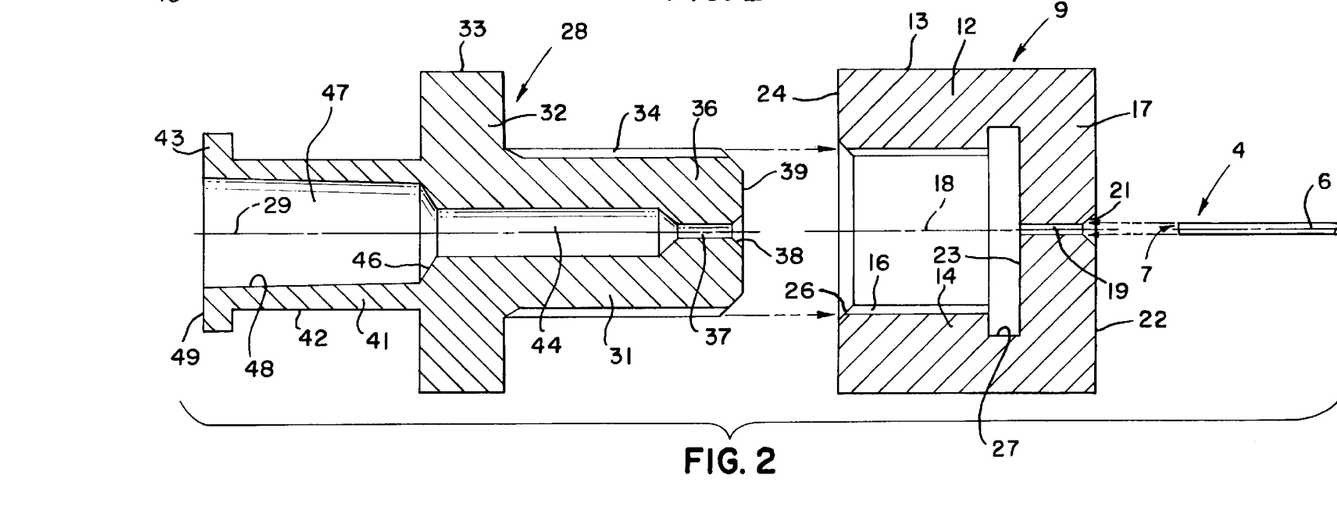
FIG. 2 is an enlarged cross-sectional view illustrating two portions of the detachable infusion port assembly in exploded form and shown in relation to an associated portion of the elongated flexible metallic cannula forming the catheter/guide wire, shown in elevation.
Figure 3:
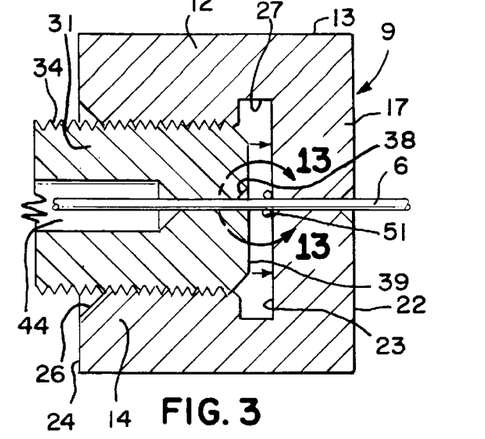
FIG. 3 is an enlarged fragmentary cross-sectional view of the detachable infusion port assembly shown assembled and just prior to sealing engagement with an associated portion of the elongated flexible metallic cannula of the catheter/guide wire.
Figure 4:
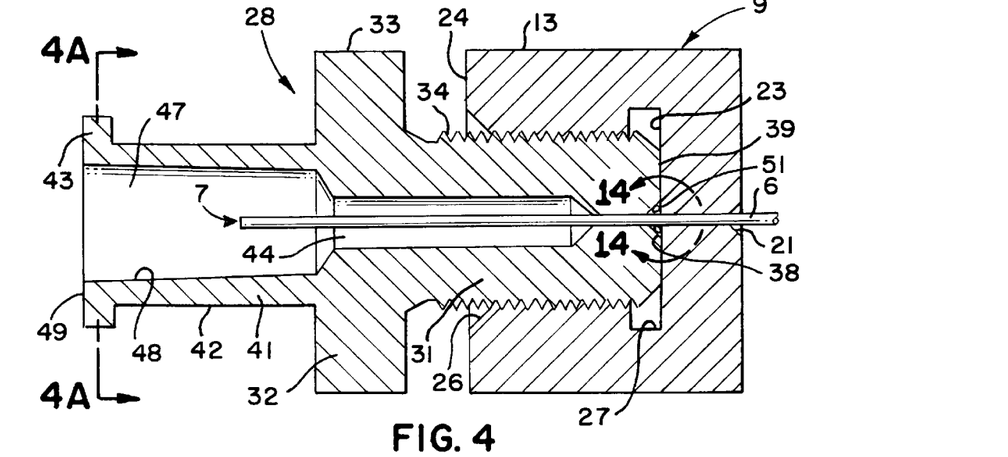
FIG. 4 is an enlarged fragmentary view illustrating the manner in which the infusion port segment is sealingly engaged to the associated proximal end portion of the elongated flexible cannula that resides within the infusion port segment.
Figure 4A:
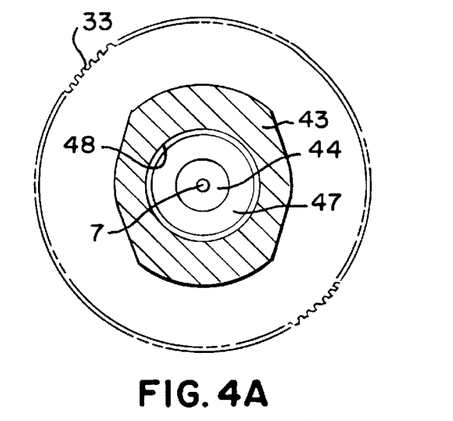
Figure 5:
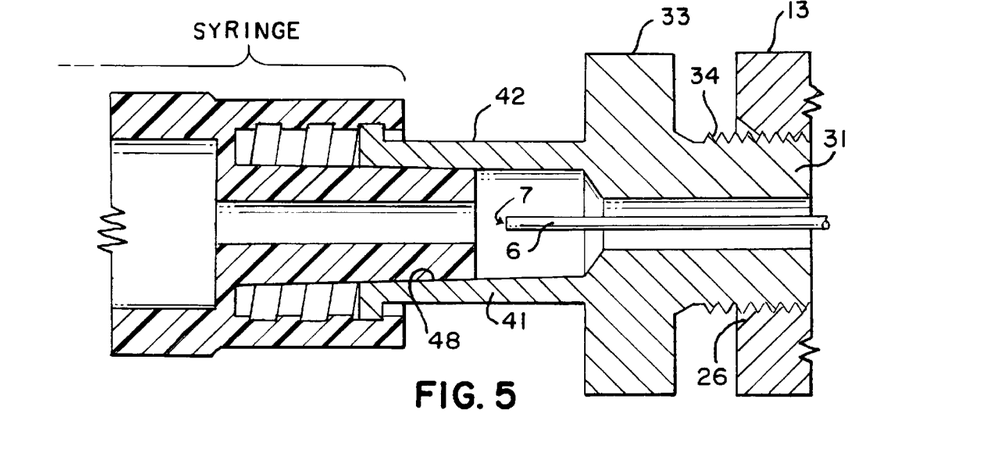
FIG. 5 is a fragmentary cross-sectional view showing the threaded end portion of a syringe detachably engaged to the infusion segment and illustrating the manner in which fluid and/or fluid-like medicaments are sealingly injected into the proximal open end of the elongated flexible metallic cannula for dispsersion under pressure from the flexible distal end segment of the catheter/guide wire structure.

Referring to FIGS. 2, 3, 4 and 5, the infusion port subassembly 3 is comprised of three interrelated and cooperative elements. One of these is a generally cylindrical gland 9 which functions, when assembled and during use of the catheter, as the "torquer" or element that is manipulated to effect rotation of the catheter within the artery as an aid to navigation through tortuous pathways. The manner of its sealing interengagement with the outer periphery of the elongated flexible metallic cannula 4 will be explained hereinafter. As illustrated in FIG. 3, gland 9 is provided with a cylindrical wall 12 having a knurled outer periphery 13 and an inner peripheral portion 14 having miniature screw threads 16 formed thereon.

The cylindrical wall 12 of the gland is closed at its distal end by a transverse end wall 17. Both the cylindrical wall 12 and the threads 16 are concentric about a longitudinal axis 18, and the end wall 17 is provided with a bore 19 that is intercepted at its distal end by a forty-five degree chamfer 21 formed in the distal surface 22 of the wall, and intercepted at its proximal or opposite end by the wall surface 23. The proximal end surface 24 of the gland is provided with a chamfer 26 that intercepts the inner peripheral portion 14 of the gland. It is important that the threads 16 and the bore 19 be concentric in relation to the longitudinal axis 18 for reasons which will become apparent. Additionally, at its distal end, the inner peripheral portion 14 is intercepted by an annular groove 27 that provides the necessary relief for the tap that forms the miniature threads 16.

To provide some sense of the small size of the gland 9, it is noted that the diameter of the knurled surface 13 is nominally ½ inch, while the diameter of the bore 19 is 0.47 mm which equates with 0.0185". Stated in other words, the bore 19 is formed by use of a Guhring No. 301 metric drillbit. The threaded Inner peripheral portion 14 possesses a thread root diameter of ¼" when threaded with 28 National Fine (NF) threads. The overall length of the gland from the distal surface 22 to the proximal surface 24 is only 0.400", while the distance from the proxmimal surface 24 to the surface 23 is only 0.280". The gland 9 is preferably precision machined from stainless steel, but may also be precision machined from aluminum and provide satisfactory results.

The second element of the infusion port sub-assembly is illustrated in FIG. 2, and comprises an infusion port fitting designated Generally by the numeral 28, and which is adapted to threadably engage the threads 16 of the gland 9 in a manner and for a purpose which will be explained hereinafter. Referring to the drawings, the fitting is precision machined from stainless steel or aluminum, and comprises an elongated monolithic structure that is symmetrical with respect to a longitudinal axis 29, and having an overall length of about 0.840".

The fitting is formed with a cylindrical distal end portion 31 having a diameter of about 0.250", and is integral at its opposite proximal end with a radially outwardly extending cylindrical flange 32 having a diameter of about 0.5", and a thickness in the longitudinal direction of about 0.125". The cylindrical flange 32 is generally positioned medianly with respect to the overall length of the fitting 28, and includes a cylindrical periphery 33 that is preferably knurled to facilitate digital manipulation. The outer cylindrical periphery of the cylindrical portion 31 is provided with threads 34 that correspond to threads 16 on the gland 9 so that the cylindrical portion 31 may be threadably engaged with the gland.

The cylindrical portion 31 is provided at its distal end with an end wall 36 having a thickness in the longitudinal direction of 0.108". The wall 36 is provided with a precision bore 37 concentric with the longitudinal axis, and conveniently formed by use of a Guhring No. 301 metric drillbit to provide a diameter of 0.47 mm (0.0185"), this being the same diameter as the bore 19 in the gland 9. The bore is provided with a chamfer 38 that defines a right-angled recess in the distal end surface 39 of the cylindrical portion 31 for a purpose which will be explained hereinafter.

Proximally from the medianly positioned cylindrical flange 32, the fitting extends integrality and longitudinally in a tubular portion 41 having a cylindrical outer periphery 42 intercepted at its proximal end by an asymmetrical radially extending flange 43 hat measures 0.308" in one direction and 0.265" in a perpendicular direction. This asymmetrical configuration of the flange 43 enables detachable attachment of related Infusion equipment. The fitting is precision machined to provide a longitudinally extending and generally cylindrical axially concentric bore 44 within the fitting that extends from about the proximal surface of the cylindrical flange 32 to the distal wall 36, where it terminates in a tapered end surface that intercepts the bore 37 as shown.

At its proximal end, the bore 44 communicates by means of a diverging intermediate conical wall portion 46 with the distal end of a larger bore 47 that is symmetrically formed about the longitudinal axis 29, and is provided with a radially outwardly diverging (tapered) inner peripheral surface 48 that is intercepted by the proximal end surface 49 of the fitting which also defines the proximal end surface of the asymmetrical flange 43.

It will thus be seen that when the fitting 28 is threaded into the gland 9, the distal end surface 39 of the fitting 28 approaches the proximal wall surface 23 of the gland. It will also be understood that because of the high precision with which both the fitting and the gland are machined, the longitudinal axis 29 of the fitting will be coincident with the longitudinal axis 18 of the gland. Because of this relationship, and because the bore 37 in the fitting is exactly the same diameter as the bore 19 in the gland 9; it will be seen that the two bores, though separated longitudinally, are precisely in axial alignment.

Figure 13:
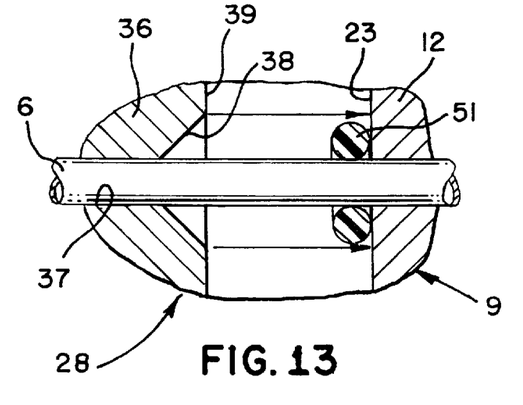
FIG. 13 is an enlarged fragmentary cross-sectional view illustrating the relationship between the infusion port assembly, including the "O" ring surrounding the cannula prior to sealing attachment of the infusion port assembly to the cannula.
Figure 14:
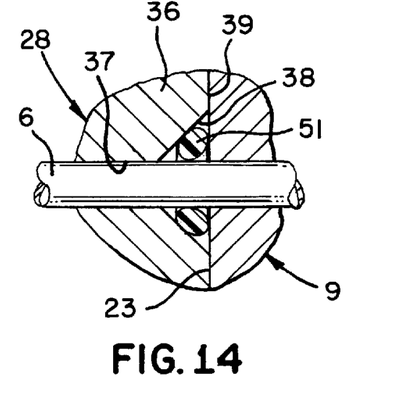
FIG. 14 is a view similar to FIG. 13, but Illustrating the relationship after the "O" ring is sealingly compressed about the cannula.

Referring to fragmentary FIGS. 13 and 14, it will be seen that when an appropriately dimensioned resiliently compressible "O"-ring 51 is disposed in the conically tapered recess formed by the chamfer 38, and the fitting 28 and gland 9 are threaded together to cause the distal end surface 39 of the fitting to approach the proximal wall surface 23 of the gland 9, the outer periphery of the "O"-ring will come into contact with and be compressed by proximal surface 23 into the conically tapered recess formed by the chamfer 38, and in so doing will cause radially inward constriction of the inner periphery of the "O"-ring so that, absent an obstruction, the diameter of the inner periphery of the "O"-ring will diminish to less than the diameter of the bores 37 and 19.

Should an obstruction, such as a cylindrical rod or tube be inserted concentrically into the bores 37 and 19, it will be seen that as the surface 23 presses against the "O"-ring, both the outer and inner peripheries of the "O" ring will be constricted until the inner periphery impinges the rod or tube. Continued compression of the "O"-ring by continued relative rotation of the gland and the fitting will increase the area of contact of the "O"-ring with the rod or tube, and will increase the force with which the inner periphery of the "O"-ring engages the outer periphery of the rod or tube.

By careful selection of the diameter of the "O"-ring, it will be seen that the compressed "O"-ring may ultimately be fully contained within the recess formed by the chamfer, and that the distal end surface 39 of the fitting may contiguously abut the proximal surface 23 of the gland so as to essentially lock these two members together against inadvertent relative rotation to back the gland away from the fitting and release the "O"-ring and the rod or tube.

In connection with the instant invention, the "obstruction" referred to above, and the interaction of that obstruction with the infusion port sub-assembly 3, is formed by the proximal end portion 6 of the elongated flexible metallic cannula 4 being inserted initially through the bore 19 that opens through chamfer 21 formed in the distal end surface 22 of the gland 9. The proximal end portion of the cannula is then inserted through the appropriately dimensioned "O"-ring 51, and subsequently is inserted by way of chamfer 38 in distal end surface 39 of the fitting 28 into and through the bore 37.

The elongated flexible metallic cannula 4 is formed from an alloy of nickel and titanium and is marketed under the trademark "NITINOL". Some of its very important characteristics are that it is flexible, kink resistant, superelastic, and possesses "shape memory". It also possesses superior bursting strength (above 250 psi), may be fabricated in single or multi-lumen form in substantially filament diameters in the order of from about 0.008" to 0.40", yet possesses sufficient columnar strength to enable relatively long lengths of the cannula, with attached distal flexible segment, to be navigated and propelled along small diameter arteries and vascular side-branches without danger of kinking or collapsing.

With a wall thickness of from 0.002" to 0.004", it also possesses sufficient torsional strength to enable the elongated flexible metallic cannula to be rotated from its proximal end so as to effect rotation of the distal end of the catheter in the same direction and by essentially the same angular amount, thus further aiding in the navigation of the catheter along tortuous pathways to effect delivery of fluid or fluid-like mediums to a target tissue site. Additionally, the elongated cannula may be "coiled" into a relatively small diameter multi-turn unit without the risk that it will kink, or that it will not elongate when "uncoiled". This characteristic is an important consideration when designing packaging, since the completed catheter may be "coiled", packaged and stored for future use in a relatively small space.

Figure 1:
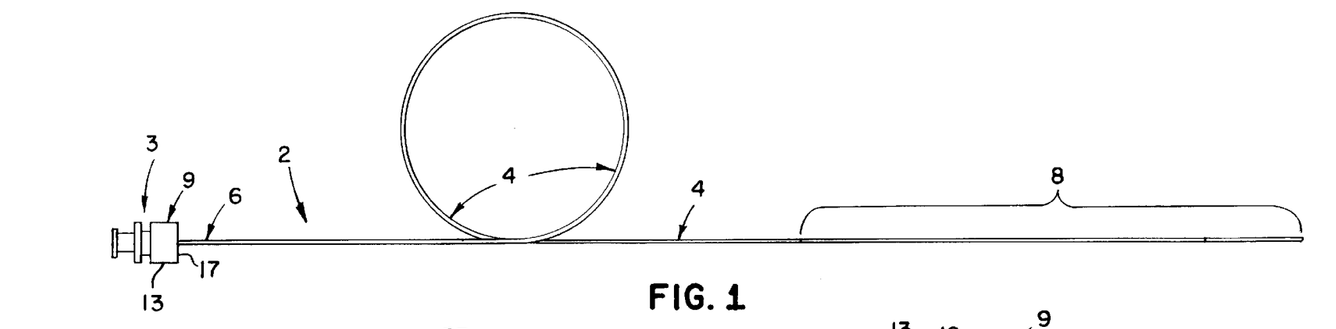
FIG. 1 is an overall elevational view of the steerable infusion catheter/guide wire assembly illustrating a portion of the flexible metallic cannula segment coiled to reduce the length of the figure.
Figures 6, 7:
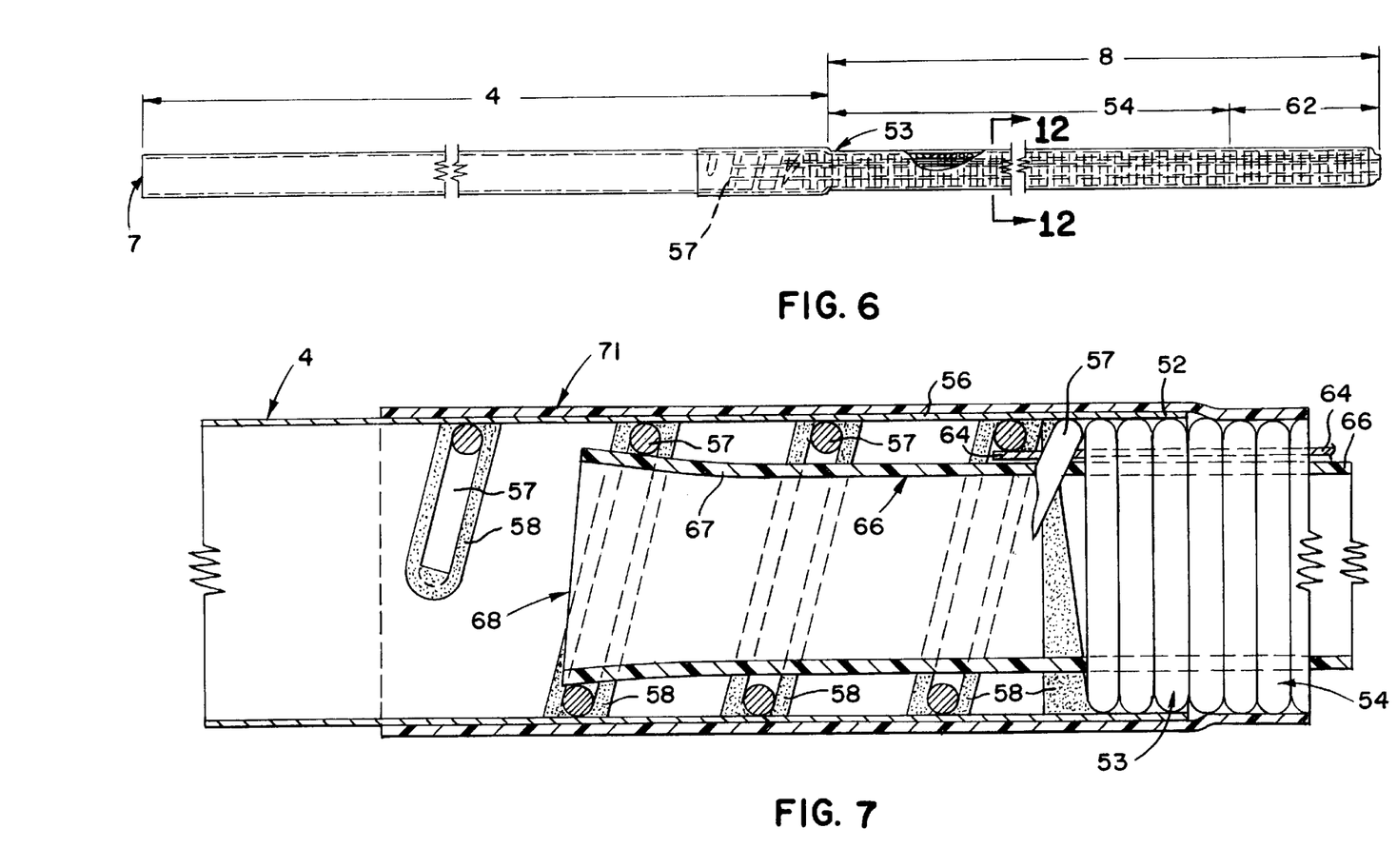
FIG. 6 is an elevational view of the distal end portion of the elongated flexible cannula connected in axial alignment to the proximal end of the flexible distal end segment of the catheter. A portion of the cannula and a portion of the flexible distal end segment have been removed to shorten the view.
FIG. 7 is an enlarged fragmentary cross-sectional view illustrating the axially concentric interconnection of the distal end portion of the elongated flexible metallic cannula to the proximal end turns of an associated flexible metallic coil, flexible inner and outer tubes, and a portion of the thin metal strip, one end of which is shown connected to an associated coil turn.

Referring to FIGS. 1 and 6, it will be seen that the complete length of the catheter, from its proximal end that includes the infusion port sub-assembly 3 to the distal end of the flexible segment, can be at least 175 cm (68.89"), with the flexible cannula 4 comprising approximately 70–95% of this length and in this instance being approximately 150 cm or 61" long, with the distal flexible segment 8 completing the remainder of the length of about 20 cm (7.8") long.

Thus, the proximal end portion 6 of the cannula 4 is advanced sequentially through bore 19, through "O"-ring 51, through bore 37, and into the bore 44 for whatever length is necessary to enable the open end 7 of the cannula within the bore 44 to be accessed by a fluid or fluid-like medicament injection instrument to enable such medicament to be pumped under pressure through the cannula to the distal end thereof where it communicates with the distal flexible segment of the catheter, from whence, as will be seen, the medicament is dispersed into the target tissue.

In that regard, reference is made to FIGS. 1 and 7, wherein the distal end 52 of the cannula 4 is illustrated connected to the associated proximal end 53 of the flexible distal segment 8 of the catheter. It is noted that the illustration is greatly enlarged to provide clarity in the relationship of the actually very small components. Thus, the flexible distal segment 8 is comprised of five separate components interrelated to produce an elongated flexible and bendable segment that includes a proximal stainless steel coil 54 the proximal end of which is secured to the inner periphery of the distal end portion 56 of the cannula 4 as illustrated in FIG. 7.

The coil 54 is normally wound with contiguous adjacent turns wound from stainless steel wire or ribbon that has a thickness of approximately 0.003", the coil thus formed having an outside diameter that may range from about 0.008" to 0.040". To attach the proximal end turns 57 of the coil to the inner periphery of the associated end portion of the cannula, the coil turns are pulled apart from their normal contiguous relationship and coated with an appropriate ultraviolet adhesive 58 such as Dymax 186M Gel available from the Dymax Corporation. The three or four axially spaced end turns 57 are then inserted into the open distal end of the cannula, together with five or six of the contiguous turns of the coil, which are also coated with the adhesive. Upon curing, the adhesive retains the end of the coil securely within the distal end portion of the cannula.

Figures 8, 9:
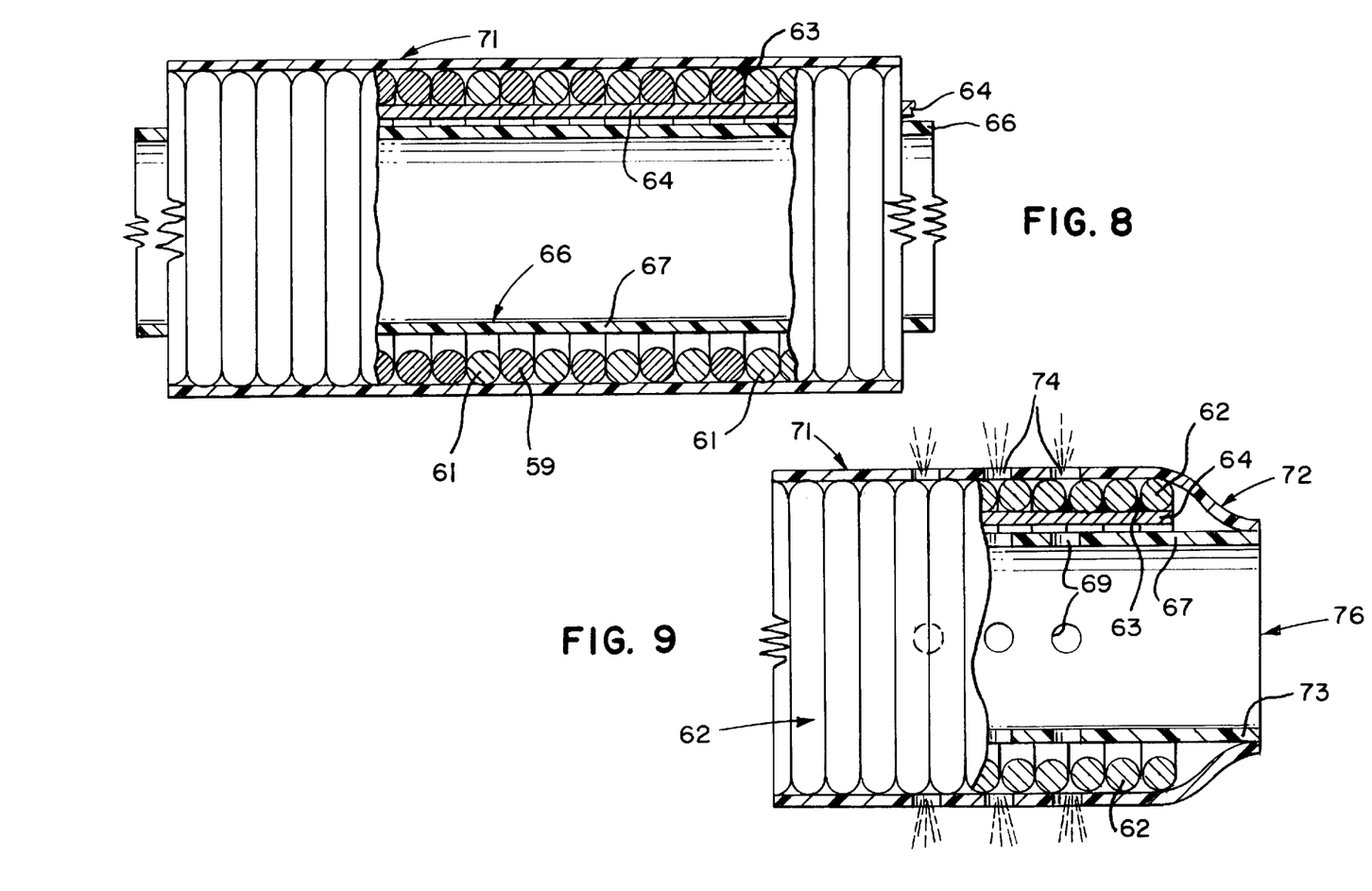
FIG. 8 is an enlarged fragmentary cross-sectional view illustrating the interconnection of the distal end turns of the flexible metallic coil illustrated in FIG. 7 intertwined with the proximal end turns of the radio-opaque coil.
FIG. 9 is an enlarged fragmentary cross-sectional view illustrating the terminal end portion of the flexible distal end segment of the catheter/guide wire.

At its opposite or distal end, a number of the end turns 59 of the coil 54 are intertwined with the associated end turns 61 of the distal coil 62 and the intertwined end turns 59 are soldered contiguously to the intertwined turns 61 as shown by the fillits 63 formed between the turns, here shown enlarged for clarity. Instead of solder, adhesive may also be used. It should be noted that the distal coil 62 is wound from a radio-opaque wire or ribbon such as platinum-iradium so that when the radio-opaque coil progresses through an artery its position may be viewed under fluoroscopy or other equivalent method.

It is important that the distal segment of the catheter including the proximal coil 54 and the axially aligned and intertwined distal radio-opaque coil 62 be flexible. It is also important that it possess columnar strength, and that the extreme end portion of the distal coil be susceptible to be bent into a substantial "J" configuration, and that it remain in such configuration during insertion and progression in an artery, and that it be susceptible of being straightened to eliminate the "J" configuration once removed from the artery.

Figures 10, 11:
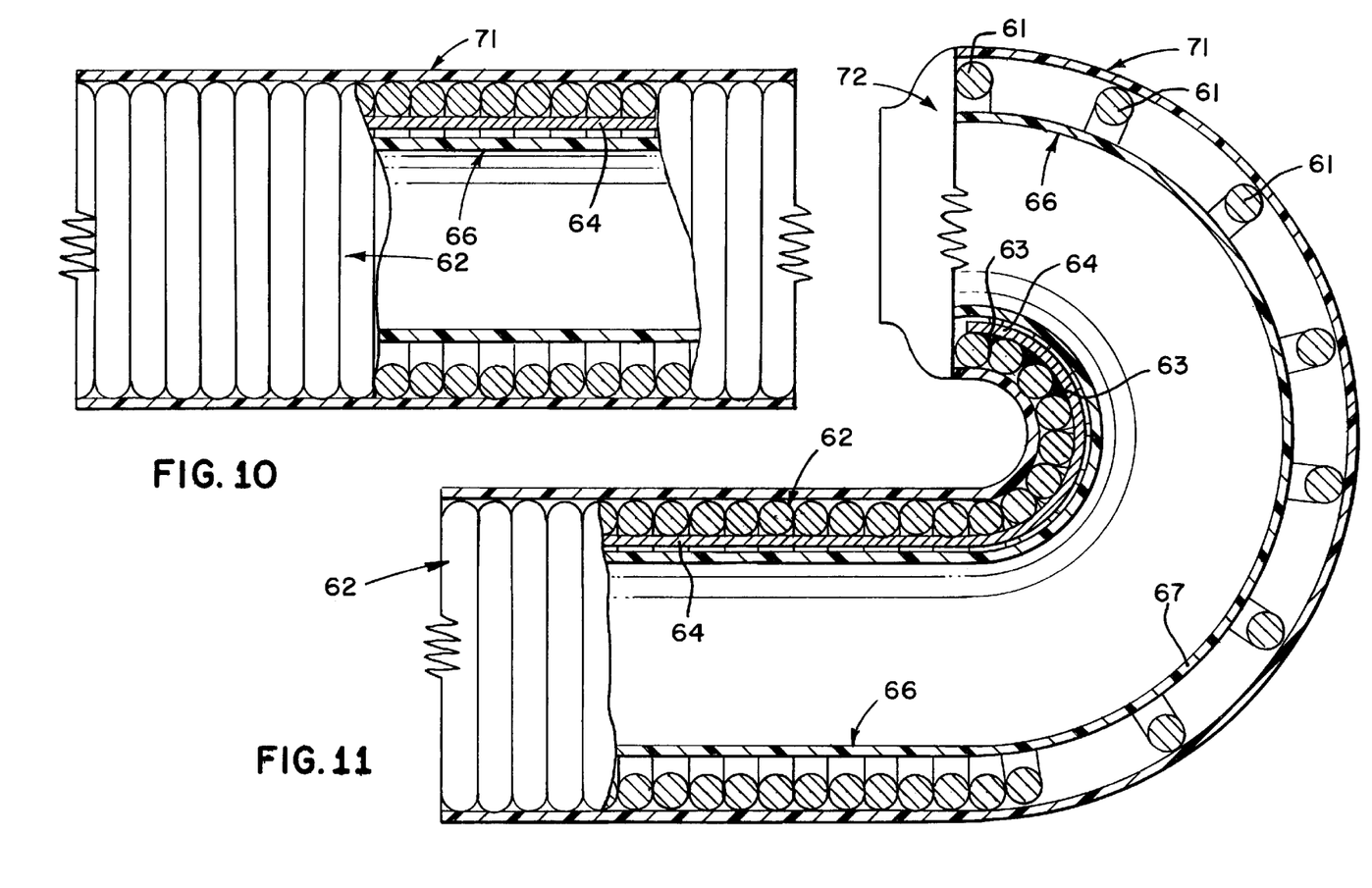
FIG. 10 is an enlarged fragmentary cross-sectional view illustrating the elongated bendable metallic strip embedded in the flexible distal end segment of the catheter/guide wire that enables selective curvature of the distal end segment to facilitate navigation of the distal end segment through tortuous pathways formed by small vasculature.
FIG. 11 is an enlarged fragmentary cross-sectional view similar to FIG. 10 but showing the flexible distal end segment selectively curved adjacent its terminal end and retained in this configuration by the bendable metallic strip.
Figure 12:
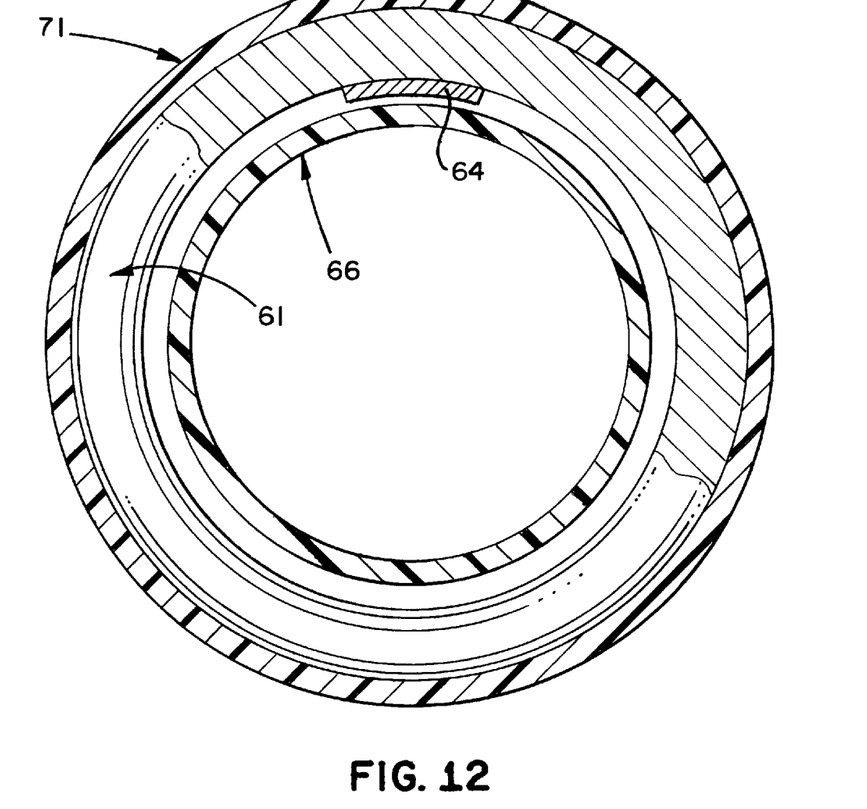
FIG. 12 is an enlarged cross-sectional view taken in the plane indicted by the line 12—12 in FIG. 6.

To effect this end, the flexible distal segment is provided over its entire length with a thin elongated reinforcing wire 64 one end of which is attached as by soldering to the end turn of the radio-opaque coil 62, the remainder of the reinforcing wire extending proximally to the distal end of the cannula 4, where it is secured by adhesive of the type previously discussed. The re-inforcing wire is preferably a flat strip of stainless steel that may be bent and shaped without breaking, and which will retain its shape once formed until it is re-shaped to a different configuration, in this environment, it has been found that a stainless steel wire ribbon having a thickness ranging from 0.0003" to 0.0015, and a width ranging from 0.0001 to 0.0015" is adequate to achieve the purpose of "shapeability" of the distal end portion of the coil 62 it will of course be understood that under some circumstances other dimensions for the flat reinforcing wire may be more appropriate. When necessary to retain the flat reinforcing wire parallel with the longitudinal axis of the flexible distal segment, it may be attached at several points along is length to the underlying turns of the coils 54 and 62.

To further reinforce the flexible distal segment of the catheter including the two coils 54 and 62, there is provided within the coextensive coils 54 and 62, an inner tube 66 about 12" long that projects distally beyond the last turn of the radio-opaque coil 62 about 0.003". The inner tube 66 provides a generally cylindrical elastic wall 67 the outer periphery of which is contiguous with the inner peripheries of the coils 54 and 62, and which also extends in the opposite or proximal direction into the distal end portion 56 of the cannula 4, where an open proximal end portion 68 of the inner tube 66 is secured by adhesive to the inner peripheries of the coil turns 57 and to the associated and surrounding inner periphery of the distal end portion of the cannula to which the coil turns 57 are adhered. The inner tube is conveniently formed from a flexible and elastic polymide material having a wall thickness ranging from 0.0005" to 0.040" and having an outer diameter ranging from 0.008" to 0.030". Other suitable materials and dimensions may of course be selected, and the inner tube may selectively be formed from a single or multi-lumen wall structure. In addition to reinforcing the flexible distal segment of the catheter, it will be understood that the inner tube also functions as a liner to prevent fluid or fluid-like medicaments from being dispersed between the turns of the coils 54 and 62 in the absence of radially directed apertures 69 formed in the wall 67 of the inner tube for that purpose as will hereinafter be explained.

To further insure that fluid or fluid or fluid-like medicaments are prevented from being dispersed radially between the turns of coils 54 and 62 in the absence of apertures 69 appropriately formed in the inner tube for that purpose, there is provided an outer tube designated generally by the numeral 71, preferably formed from a heat shrinkable material such as polyester. The outer tube is of sufficient length to envelope the entire length of the flexible distal segment of the catheter and to provide at its distal end an overlapping portion 72 that surrounds the protruding distal end portion 73 of the inner tube beyond the last turn of the coil 62, to the outer periphery of which protruding distal end portion 73 the closely surrounding distal end portion 72 of the outer tube is sealed as by adhesive or other suitable means of sealing. It will of course be understood that after slipping the close-fitting polyester outer tube over the flexible distal segment, application of appropriate heat over the length of the outer tube will cause it to shrink radially and to closely adhere to the outer peripheries of the coils 54 and 62 and a portion or the outer periphery of the distal end portion of the cannula over which the outer tube also extends.

The heat-shrinkable polyester outer tube forms a smooth transition between the distal end of the cannula and the flexible distal segment. The outer tube may be formed with a wall thickness ranging from 0.0005 to 0.002", and is also provided with radially directed apertures 74 that cooperate with corresponding radially directed apertures 69 in the wall of the inner tube, to disperse fluid or fluid-like medicaments radially from the outer end portion of the flexible distal segment in addition to dispersing it from the open distal infusion end 76 of the inner tube. Additionally, the outer tube 71 also functions to prevent body fluids from entering the flexible distal infusion segment of the catheter, and provides a safety function for any potential dislodgment of the components that make up the flexible distal segment, or dislodgment of the entire flexible distal segment from the distal end portion of the cannula. This insures that such dislodged segment or component may be retrieved without undue difficulty and certainly without the need of an additional surgical procedure.

As indicated above, the entire length of the flexible cannula with attached flexible distal segment may be coated with a lubricious layer of silicon based lubricant or a hydrophilic layer to minimize friction when the entire catheter/guide wire is itself utilized as a guide wire and another appropriate catheter is introduced over the steerable infusion catheter/guide wire of the present invention. Additionally, the catheter/guide wire may be coated with thrombolitic agents such as heparin to minimize the possibility of thrombus formation during the use.

Having thus described the invention, what is believed to be novel and sought to be protected by letters patent of the Unites States is as follows.

I claim:

1. A steerable infusion catheter/guide wire, comprising:
   a) an elongated cannula symmetrical about a longitudinal axis and having open proximal and distal end portions;
   b) an infusion port assembly symmetrical about said longitudinal axis and sealingly secured detachably to said proximal end portion of said cannula and digitally rotatable to correspondingly rotate said elongated cannula over its entire length; and
   c) a flexible distal segment including means interrelated to provide an elongated bendable tubular member generally symmetrical about said longitudinal axis and having an open proximal end portion and an open distal end portion, said open proximal end portion having its open proximal end concentrically secured within the open distal end portion of said elongated cannula.

2. The steerable infusion catheter/guide wire according to claim 1, wherein said elongated cannula is metallic.

3. The steerable infusion catheter/guide were according to claim 1, wherein said elongated cannula is fabricated from an alloy of nickel and titanium.

4. The steerable infusion catheter/guide wire according to claim 1, wherein said elongated cannula possesses a uniform diameter over its entire length.

5. The steerable Infusion catheter/guide wire according to claim 1, wherein said cannula has an outer diameter of approximately 0.018".

6. The steerable infusion catheter/guide wire according to claim 1, wherein said catheter is approximately 175 centimeters in overall length.

7. The steerable infusion catheter/guide wire according to claim 1, wherein said cannula is approximately 155 centimeters in overall length.

8. The steerable infusion catheter/guide wire according to claim 1, wherein said flexible distal segment extends approximately 20 centimeters from the open distal end portion of said cannula.

9. The steerable infusion catheter/guide wire according to claim 1, wherein said open distal end portion of said flexible distal segment comprises radio-opaque material.

10. The steerable infusion catheter/guide wire according to claim 1, wherein said open proximal end portion of said flexible distal segment comprises a stainless steel coil a plurality of the proximal turns of which are spaced apart and concentrically secured within the open distal end portion of said elongated cannula.

11. The steerable infusion catheter/guide wire according to claim 1, wherein said open proximal end portion of said flexible distal segment comprises a stainless steel coil and said open distal end portion of said flexible distal segment comprises a radio-opaque coil both symmetrical about said longitudinal axis.

12. The steerable infusion catheter/guide wire according to claim 1, wherein said means of said flexible distal segment interrelated to provide a bendable tubular member includes an elongated non-metallic flexible inner tube the proximal open end portion of which is sealingly attached to the inner periphery of said distal end portion of the cannula.

13. The steerable infusion catheter/guide wire according to claim 1, wherein said means of said flexible distal segment interrelated to provide a bendable tubular member includes an elongated bendable metallic strap parallel to said longitudinal axis and laterally spaced therefrom.

14. The steerable infusion catheter/guide wire according to claim 1, wherein said means of said flexible distal segment interrelated to provide a bendable tubular member includes an elongated non-metallic flexible outer tube the proximal end portion of which is sealingly attached concentrically about the distal end portion of said cannula and the distal end portion of which outer tube is sealingly attached concentrically about the open distal end portion of said flexible distal segment.

15. The steerable Infusion catheter/guide wire according to claim 11, wherein said stainless steel and radio-opaque coils include coil turns that are axially aligned and at least one of the distal end turns of said stainless steel coil is intertwined with and attached to the associated proximal end turns of the radio-opaque coil.

16. The steerable infusion catheter/guide wire according to claim 15, wherein a plurality of the proximal turns of said stainless steel coil are spaced apart and concentrically secured within the open distal end portion of said elongated cannula, an elongated non-metallic flexible inner tube disposed concentrically within and spanning the length of said stainless steel and radio-opaque coils, a proximal end portion of said inner tube sealingly attached to said spaced stainless steel coil turns and to the inner periphery of said distal end portion of said elongated cannula and a distal end portion of said inner tube projecting out of the open distal end of said radio-opaque coil, an elongated bendable metallic strip parallel to said longitudinal axis and interposed between the outer periphery of said inner tube and the inner peripheries of said stainless steel and radio-opaque coils, the proximal and distal end portions of said metallic strip being attached to corresponding associated end portions of said coils and an intermediate portion of said bendable metal strip being attached to said intertwined turns of said coils, and an elongated non-metallic flexible outer tube concentrically surrounding and sealingly attached to the distal end portion of said elongated cannula, said intertwined axially aligned coils and said projecting distal end portion of said inner tube, whereby said outer tube forms a flexible outer lumen for said flexible distal segment.

17. The steerable infusion catheter/guide wire according to claim 16, wherein a plurality of radially extending apertures are formed in said Inner and outer tubes through which a liquid or liquid-like substance may be radially dispensed under pressure into a target tissue site.

18. The steerable infusion catheter/guide wire according to claim 16, wherein said distal end portion of said cannula, said aligned coils and said bendable elongated metallic strip are sealingly encapsulated between said flexible non-metallic inner and outer tubes.

19. The steerable infusion catheter/guide wire according to claim 12, wherein said non-metallic flexible inner tube is formed from a synthetic resinous material.

20. The steerable Infusion catheter/guide wire according to claim 14, wherein said non-metallic flexible outer tube is formed from a heat-shrinkable synthetic resinous material.

21. The steerable infusion catheter/guide wire according to claim 15, wherein said intertwined turns of said proximal and distal coils are soldered to one another.

22. The steerable infusion catheter/guide wire according to claim 13, wherein said elongated bendable metallic strip is formed from stainless steel.

23. The steerable infusion catheter/guide wire according to claim 1, wherein said infusion port assembly includes a gland having a tubular cylindrical wall having attachment means on its inner periphery and generally open at one end and closed at its opposite end by a transverse end wall having proximal and distal faces and having a central bore extending therethrough symmetrical about said longitudinal axis and intercepted by said proximal and distal faces, and an infusion port fitting selectively attachable to said tubular cylindrical wall and adjustable axially in relation to said gland.

24. The steerable infusion catheter/guide wire according to claim 23, wherein said central bore in said transverse end wall is chamferred at said distal face to facilitate the entry and passage of the proximal end portion of said elongated cannula into said central bore and through said transverse end wall.

25. The steerable infusion catheter/guide wire according to claim 23, wherein said attachment means on the inner periphery of said tubular cylindrical wall comprise screw threads concentric to said longitudinal axis.

26. The steerable infusion catheter/guide wire according to claim 23, wherein said proximal face of said transverse wall intercepts the periphery of said central bore at an angle of 90 degrees.

27. The steerable infusion catheter/guide wire according to claim 23, wherein said infusion port fitting includes a central bore symmetrical about said longitudinal axis and through which said cannula projects, means on said infusion port fitting cooperating with said attachment means on said gland enabling selective relative axial displacement of said gland and said infusion sort fitting, and seal means surrounding said proximal end portion of said cannula disposed within said infusion port assembly and interposed between said gland and said infusion port fitting and elastically compressible to resiliently engage said proximal end portion of said cannula when said gland and said infusion port fitting are displaced toward one another sufficiently to compress said seal means, whereby rotation of said infusion port assembly effects a corresponding rotation of said elongated cannula and said flexible distal segment of said catheter.

28. The steerable infusion catheter/guide wire according to claim 27, wherein said infusion port fitting is provided with a distal end surface having a conical recess surrounding said proximal portion of said cannula, and said seal means is mounted in said conical recess.

29. The steerable infusion catheter/guide wire according to claim 28, wherein said seal means comprises an "O"-ring having an outer peripheral diameter approximately equal to the base diameter of said conical recess and an inner peripheral diameter closely surrounding said cannula, whereby when said "O"-ring is compressed into said conical recess by said gland both said outer and inner peripheral diameters of said "O" ring are reduced, so that said inner periphery of said "O"-ring resiliently and nonrotatably engages the outer periphery of the associated cannula whereby the entire length of said cannula and said flexible distal segment may selectively be rotated by rotation of said gland.

30. The steerable infusion catheter/guide wire according to claim 29, wherein said attachment means on said gland comprises screw threads formed on the inner periphery of said tubular cylindrical wall, and said infusion port fitting is provided with corresponding screw threads engageable therewith whereby relative rotation of said gland and said infusion port fitting effects selective relative axial displacement thereof toward or away from one another.

31. As an article of manufacture, a three-part assembly for use with elongated cylindrical members such as rods or tubes enabling slidably mounting said three-part assembly in assembled form onto said cylindrical member and thereafter selectively locking said three-part assembly immovably to said cylindrical member, comprising:

a) a gland symmetrical about a longitudinal axis and including a tubular cylindrical wall member having screw threads on its inner periphery and a transverse end wall closing one end of said tubular cylindrical member and having a bore therethrough concentric to said longitudinal axis for slidably receiving therethrough said rod or tube;

b) a cylindrical fitting symmetrical about said longitudinal axis and having a tubular member having screw threads on its outer periphery selectively engageable with said screw threads on said gland and a distal end wall having a central bore therethrough and a distal end surface having a conical recess therein communicating at its apex end with said central bore; and     c) seal means having a compressible body mounted in said conical recess so that a portion of said compressible body projects out of the base of said conical recess and having a central aperture therethrough having a diameter at least as large as the diameter of said central bore, whereby when said gland and said cylindrical fitting are rotated to advance said fitting into said gland said seal means is compressed and the diameter of said aperture through said compressible body is reduced whereby a rod or tube projecting through said aperture is resiliently impinged sealingly by said seal means, whereby said three-part assembly is locked onto a red or tube extending through said assembly.

32. The article of manufacture according to claim 31, wherein said seal means comprises an "O"-ring the outer peripheral diameter of which is approximately equal to the base diameter of said conical recess and the inner peripheral diameter is at least as large as said central bore in said distal end wall.

33. The article of manufacture according to claim 32, wherein said transverse end wall of said gland has a proximal face confronting said distal end surface of said distal end wall of said cylindrical fitting, said bores in said end walls are axially aligned, and said "O"-ring is compressed into said conical recess by the confronting proximal face of said transverse end wall of said gland when said distal end surface of said distal end wall of said cylindrical fitting abuts said confronting proximal face of said transverse wall, whereby the inner peripheral diameter of said aperture through said "O"-ring is constricted to less than the diameter of the associated bore in the absence of a rod or tube in said bore.

34. The article of manufacture according to claim 31, wherein the outer peripheral surface of said tubular cylindrical wall member is knurled.

35. The article of manufacture according to claim 31, wherein said tubular member of said cylindrical fitting constitutes the distal portion of said fitting, a radially outwardly extending flange integral with the proximal end of said tubular member, a proximal tubular portion axially aligned with said distal portion and integral with said radially outwardly extending flange, and an asymmetric radially outwardly extending lock flange integral with the proximal end of said proximal tubular portion.

\* \* \* \* \*